(12) United States Patent
Goad et al.

(10) Patent No.: US 9,500,591 B1
(45) Date of Patent: Nov. 22, 2016

(54) PLASTIC PARTICLE DETECTOR FOR DETECTION OF BIOLOGICAL AEROSOL AND OTHER FLUORESCENT MATERIALS

(71) Applicant: U.S. Army Edgewood Chemical and Biological Command, Apg, MD (US)

(72) Inventors: Aime P. Goad, Baltimore, MD (US); David W. Sickenberger, Bel Air, MD (US); Fiona E. Narayanan, Forest Hill, MD (US); Richard J. Kreis, Bel Air, MD (US); Lester D. Strauch, III, Bel Air, MD (US); Gary K. Kilper, Perry Hall, MD (US); Jerry B. Cabalo, Towson, MD (US); Harold S. Wylie, Elkton, MD (US); Anna Wong, Bel Air, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 24 days.

(21) Appl. No.: 14/678,395

(22) Filed: Apr. 3, 2015

(51) Int. Cl.
| | |
|---|---|
| G01N 21/64 | (2006.01) |
| G01N 21/47 | (2006.01) |
| G01N 15/14 | (2006.01) |
| B29D 11/00 | (2006.01) |
| B29K 77/00 | (2006.01) |
| B29K 507/04 | (2006.01) |
| B29K 509/08 | (2006.01) |

(52) U.S. Cl.
CPC ....... *G01N 21/6486* (2013.01); *B29D 11/0074* (2013.01); *G01N 15/1434* (2013.01); *G01N 21/47* (2013.01); *G01N 21/645* (2013.01); *B29K 2077/00* (2013.01); *B29K 2507/04* (2013.01); *B29K 2509/08* (2013.01); *G01N 2021/6471* (2013.01); *G01N 2201/062* (2013.01)

(58) Field of Classification Search
CPC .......... G01N 21/645; G01N 21/6486; G01N 15/1434; G01N 21/47
See application file for complete search history.

(56) References Cited

U.S. PATENT DOCUMENTS

| | | | | |
|---|---|---|---|---|
| 4,008,397 A * | 2/1977 | Zdrodowski | ....... | G01N 21/0303 250/373 |
| 5,640,463 A * | 6/1997 | Csulits | .................. | B65H 3/063 194/207 |
| 6,885,440 B2 * | 4/2005 | Silcott | ............... | G01N 15/0205 250/492.1 |
| 7,375,348 B1 * | 5/2008 | Sickenberger | ......... | G01N 15/06 250/461.2 |
| 2005/0073683 A1 * | 4/2005 | Gard | ................... | H01J 49/0445 356/337 |
| 2005/0127305 A1 * | 6/2005 | Androsyuk | ............ | G07D 7/121 250/461.1 |
| 2006/0024703 A1 * | 2/2006 | Zhang | ................. | C12Q 1/6837 435/6.11 |
| 2007/0087165 A1 * | 4/2007 | Jung | ...................... | B29C 59/14 428/141 |
| 2010/0252128 A1 * | 10/2010 | Gong | .................... | B01L 3/5025 137/561 A |
| 2011/0240886 A1 * | 10/2011 | Tokhtuev | ............. | G01N 21/645 250/461.1 |
| 2014/0273194 A1 * | 9/2014 | Handique | .......... | G01N 21/6458 435/288.7 |

\* cited by examiner

*Primary Examiner* — Marcus Taningco
(74) *Attorney, Agent, or Firm* — Ulysses John Biffoni

(57) ABSTRACT

A plastic particle detector for detecting biological and other fluorescent materials is disclosed. The detector detects the fluorescence and scattering signals from these materials using deep UV excitation. The detector is fabricated using plastic materials and exploits the properties of lower manufacturing costs, lower materials costs, light weight, ruggedness and assembly ease offered by plastics, while eliminating stray fluorescence signals ordinarily generated by plastic materials.

24 Claims, 8 Drawing Sheets

PLASTIC PARTICLE DETECTOR FOR DETECTION OF BIOLOGICAL AEROSOL AND OTHER FLUORESCENT MATERIALS

STATEMENT OF GOVERNMENT INTEREST

The invention described herein may be manufactured, used, and/or licensed by or for the Government of the United States of America.

FIELD OF THE INVENTION

The invention relates generally to particle detectors and more particularly to particle detectors made with plastic material and having lower cost and improved ruggedness.

BACKGROUND

UV (ultraviolet) induced fluorescence continues to be one of the most promising techniques for the real time detection of biological agents and other particles. A number of detectors developed around this technique have shown that UV induced fluorescence provides a means to rapidly and accurately detect biological agents at very credible limits of detection. Among these devices are the Biological Agent Warning Sensor (BAWS) developed by MIT Lincoln Laboratory, along with several others described by U.S. Pat. Nos. 5,701,012; 5,895,922 and 6,831,279. Additional devices are described in U.S. Pat. Nos. 5,999,250; 6,885,440; 6,967,338; 7,375,348; 7,567,391 and 7,852,469.

These detectors work under the principle that aerosolized biological agents will fluoresce and scatter light when excited with UV light. The UV light source can be a laser, LED with optics, or any other emission source that can produce a beam of light which can then be pointed towards aerosol particles. The excitation wavelengths are typically in the 405 to 266-nm wavelength range but are not limited to that range.

Aerosol particles will fluoresce when hit with an excitation beam due to biochemicals, specifically fluorophores, contained within the biological agents. The fluorescence is at a wavelength longer than the excitation wavelength. Tryptophan, for example, a common component of biological materials, has a peak fluorescence in the 350-nm range when excited with 266-nm light. The scattering wavelength is the same as the excitation wavelength, in this case 266-nm. Both the fluorescent and scattering light are detected using optical detectors such as a photomultiplier.

The relative amount of fluorescent and scattering light emitted from the biological aerosols can be characterized by the scattering and fluorescent cross sections ofthese materials. In general, the scattering cross sections are several orders of magnitude greater than the fluorescent cross sections.

The basic principles of detector operation are described in connection with FIG. 1A which shows a top view of a particle detector and FIG. 1B which shows a side view of a detector. Referring to FIG. 1A, a source 10 of UV light generates a UV beam 12 which intersects at 14 with a stream 16 of particles being pulled into the detector. Intersection 14 occurs within a mirrored chamber 18. A beam dump 20 captures excess light from beam 12 so that it is absorbed and removed. As shown in FIG. 1B, the intersection 14 between UV beam 12 and particle stream 16 generates scattered and fluorescent light beam 22. Beam 22 enters the region of the particle detector that transmits the scattering and fluorescence signals from the particle to the photomultiplier optical detectors. This includes beam splitter 24 which divides the beam into scattered component 26 and fluorescent component 28. Filter 30 removes extraneous scattered light from fluorescent component 28. Photomultiplier 32 records the intensity of scattering component 26 while photomultiplier 34 records the intensity of fluorescent component 28. While this device is described using photomultipliers; other optical detectors such as avalanche photodiodes (APDs) may be used. FIGS. 1A and 1B depict a general overview of particle detector operation; many other components could be used as needed for a specific situation.

A great deal of design effort has been employed to attenuate the amount of stray excitation light that can inadvertently make it to photomultipliers 32 and 34 via the optical train. The optical train of a particle detector includes all internal surfaces that have a direct or indirect path between light source 10 and photomultipliers, or optical detectors 32 and 34.

Stray light within the optical train can have two effects. First it can be falsely recorded as a scattering signal given that stray light and excitation light are both at the same wavelength. This signal will then appear as a scattering signal in scattering photomultiplier 32. Second, and more importantly, the scattered light can cause other objects and materials in the overall optical train to fluoresce. This signal will then appear as a fluorescent signal in the fluorescent photomultiplier 34.

Two main ways in which stray light can be attenuated are by using spatial filters and by eliminating reflective surfaces. In the prior art, reflective surfaces have been reduced by applying absorptive coatings or by increasing the volume of the optical train and placement of its components to the point that any reflected light would have an unlikely probability of reentering the pathway leading to the optical detector.

Those knowledgeable in the art of reducing stray light within optically based sensors and detectors understand that this represents a significant design challenge and, in general, the best solution is often a compromise as opposed to a perfect solution. This is caused by the fact that the sensor and detector design options are usually bounded by size, weight, and cost constraints. In principle, the entire optical train could be produced from any materials and coatings that result in an end product that addresses the need to attenuate the stray light and optical train fluorescence. In practice, however, this is often limited by cost and manufacturing constraints.

Prior art particle detectors working in the deep UV region and designed to detect biological materials typically avoid the use of uncoated plastics within the detector's optical train. This is especially true in the 266-nm region where plastics are known to fluorescence. This auto-florescence is significant and may easily mask the fluorescence from biological materials at the same wavelength. Plastics may also have reflective properties that causes undesired scattering of light throughout the optical train. In this case, they can appear as reflective surfaces and effectively act as shiny surfaces.

However, it is recognized that the plastics offer several benefits over non-plastic approaches. Compared to alternative approaches such as machined metals, plastics provide lower manufacturing and materials costs. They are also lighter, more rugged, and easier to assemble. However, the auto-florescence properties of available plastics have limited the ability to exploit these advantages.

While plastics offer some significant manufacturing, size, weight and cost advantages for an optical train, this choice of material has not been pursued in an integrated detector due to their reflective and fluorescent characteristics. Many plastics are inherently smooth and very reflective. There are, however, available techniques such as sanding to reduce this feature. A bigger impediment to the use of plastics in detectors is the fact that they inherently fluoresce when excited with UV light. Optically based detectors have been designed around the fluorescent quality of plastics. For example, Deep-UV LED and Laser Induced Fluorescence Detection and Monitoring of Trace Organics in Potable Liquids. WO 201204052 A2, teaches using detectors similar to those described in the patents listed above to detect a few parts per trillion of plastic resins in bottled drinking water and river plumes.

These and similar studies have generated a position within the detector development community that plastics cannot be used within UV based detectors, especially in regions where they could interact with the excitation light. The only noted exceptions were in applications where special plastics were used as a non-moving, solid support. The plastics were coated with immobilized binding ligands or similar materials. These coatings are known to produce an optical response when interrogated with UV light. In these cases, the plastic was not used or applied to the optical train in either the generation of the excitation source or the collection of the fluorescent and scattered light. The use was limited to an interrogated surface. For example. Ha Kim, et al. "Reusable low fluorescent plastic biochip: WO 2000055627 A1, teaches a non-auto-fluorescent solid support that is an alternative to glass that is suitable for the construction of biochips that can be employed in high-sensitivity, fluorescence detection and other methodologies. It identifies a UVT (Ultra-Violet Transmitting) Acrylic Ultraviolet Transmitting plastic, Glasfex® (now made by Spartech Polycast®) but does not teach if this material would function in the deep UV (<266-nm or lower) range necessary for the detection of biological constituents such as tryptophan. Data collected on similar acrylics in the deep UV would suggest that these materials would have unusable fluorescence levels at this and lower wavelengths. Regardless, even if it had been shown that UVT Acrylic Ultraviolet Transmitting plastic would function in the deep UV, Kim does not teach or suggest that such or similar material can be applied to the design and construction of the detector's optical train.

In principle, the adverse fluorescent properties of plastics could be overcome by applying a protective coating on the plastic thus shielding it from any light. The common practice of applying a metal coating would not, in itself, suffice given that this would introduce a higher level of reflected light into the optical train and adverse increase scattering signals. In addition, a coating with the proper reflective and fluorescent properties to use with a practical plastic optical train is not known, and it would certainly add cost and complexity to the design and manufacturing of plastic detector.

Thus, a need exists for an optical train in a particle detector that benefits from the reduced cost, lighter weight and ruggedness of plastics but does not have the disadvantages of reflectivity and fluorescing in deep UV wavelengths.

SUMMARY

The invention in one implementation encompasses an apparatus. The apparatus comprises a plastic-based detector for biological and other fluorescent materials that detects the fluorescence and scattering signals from these materials using deep UV excitation is disclosed. The detector is fabricated using plastic materials and exploits the properties of lower manufacturing costs, lower materials costs, light weight, ruggedness and assembly ease offered by plastics.

The invention in a further embodiment encompasses a particle detector, having an excitation region including a first plastic housing and an excitation source for generating light to excite particles passing through the particle detector; an interrogation region including a second plastic housing, for producing an emission beam from one or more particles excited by light from the excitation source; and a detection region for receiving the emission beam and including one or more optical detectors configured to determine light scattering and fluorescence properties of particles, and a third plastic housing.

In a further embodiment, the excitation region includes one or more lenses to collect light from the excitation source fitted into said first housing adjacent to the excitation source; and one or more filters fitted into the opposite end of the first housing from the excitation source to remove stray light from the excitation source.

In a further embodiment, the interrogation region includes a cavity within said second housing, said first housing attached to one side of said second housing and said third housing attached to said second housing at a position perpendicular to said first housing; and a beam dump attached to said second housing opposite said first housing.

In a further embodiment, the second housing includes embedded attachment points that mate with those on the first and third housing; embedded attachment points that mate with those on inlet and exhaust pitot tubes on opposite sides of said cavity; and embedded attachment points that mate with those on the beam dump.

In a further embodiment, the detection region includes a beam splitter for splitting the emission beam into two portions; a first optical detector configured to determine radiation scattering properties of particles passing through the particle detector according to a first portion of the emission beam; and a second optical detector configured to determine fluorescence properties of the particles passing through the particle detector according to a second portion of the emission beam.

In yet another embodiment, the invention encompasses a method of manufacturing a plastic particle detector including the steps of forming a first housing from plastic, said first housing including molded structures to hold an excitation source and one or more optical devices for focusing light from the excitation source on a particle; forming a second housing from plastic, said second housing including molded structures wherein said focused light from said excitation source intersects with said particle and generates an emission beam, said first housing attached to one side of said second housing; and forming a third housing from plastic, said third housing attached to said second housing perpendicularly to said first housing, said third housing receiving the emission beam and including molded structures for attaching two or more optical detectors; wherein said first, second and third plastic housings contain embedded fasteners so that the housings can be assembled to form the particle detector without additional hardware, glue or welding.

In a further embodiment, the method includes the step of forming a beam dump from plastic, said beam dump attached to said cavity opposite said first housing, without requiring the use of additional fasteners.

In any of the above embodiments, the plastic housings of the particle detector are formed from an uncoated plastic that does not interact with light from the excitation source to produce fluorescent light beams or scattering light beams that will be detected by the one or more optical detectors for example, a polyamide 66 resin with glass and carbon black fill.

In any of the above embodiments, the plastic housings of the particle detector are injection-molded.

In any of the above embodiments, the plastic housings of the particle detector contain embedded fasteners so that the housings can be assembled to form the particle detector without additional hardware, glue or welding.

In any of the above embodiments, the one or more optical detectors are photomultipliers or avalanche photodiodes.

In any of the above embodiments, the excitation source generates light in the deep UV wavelength range.

DESCRIPTION OF THE DRAWINGS

Features of example implementations of the invention will become apparent from the description, the claims, and the accompanying drawings in which:

DETAILED DESCRIPTION

If used and unless otherwise stated, the terms "upper," "lower," "front," "back," "over," "under," and similar such terms are not to be construed as limiting the invention to a particular orientation. Instead, these terms are used only on a relative basis.

Figure 1A:
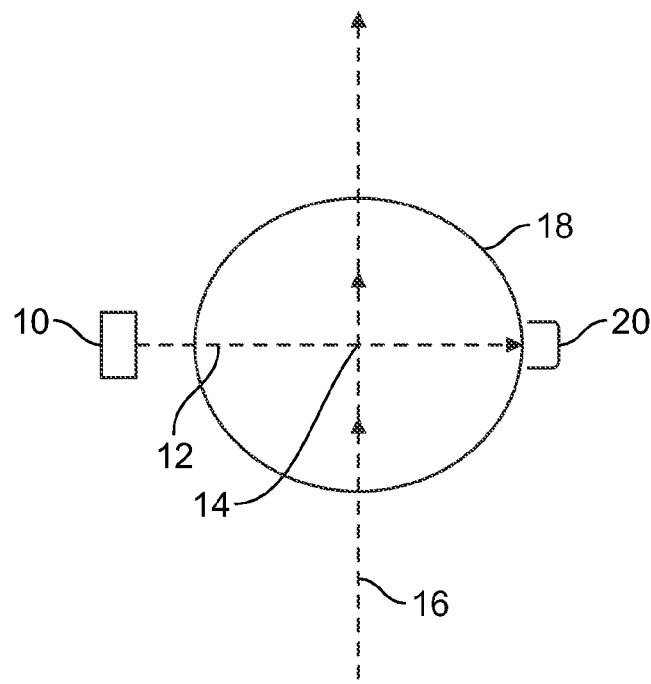
FIGS. 1A and 1B are top and side views illustrating the basic operation of a particle detector.
Figure 1B:
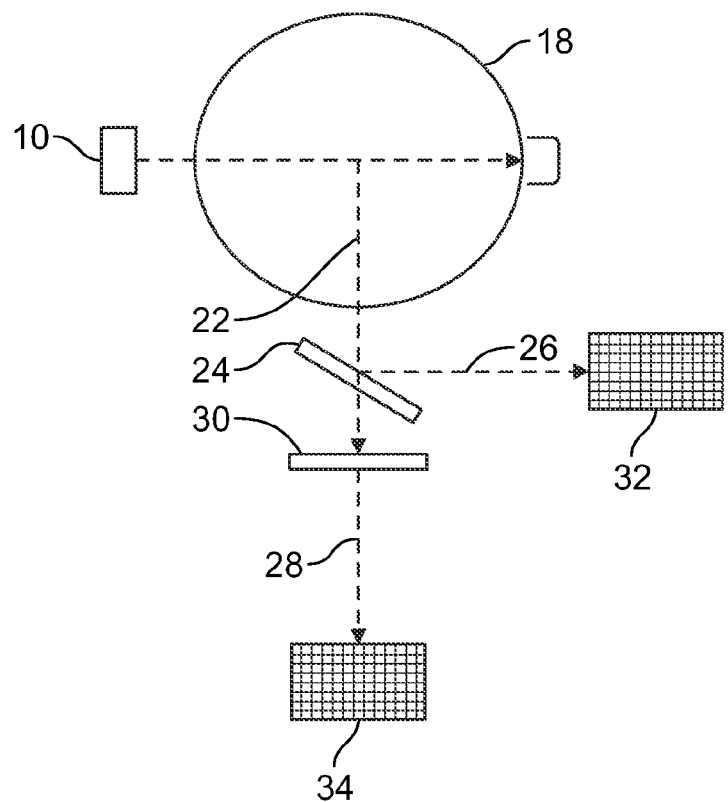
Figure 2:
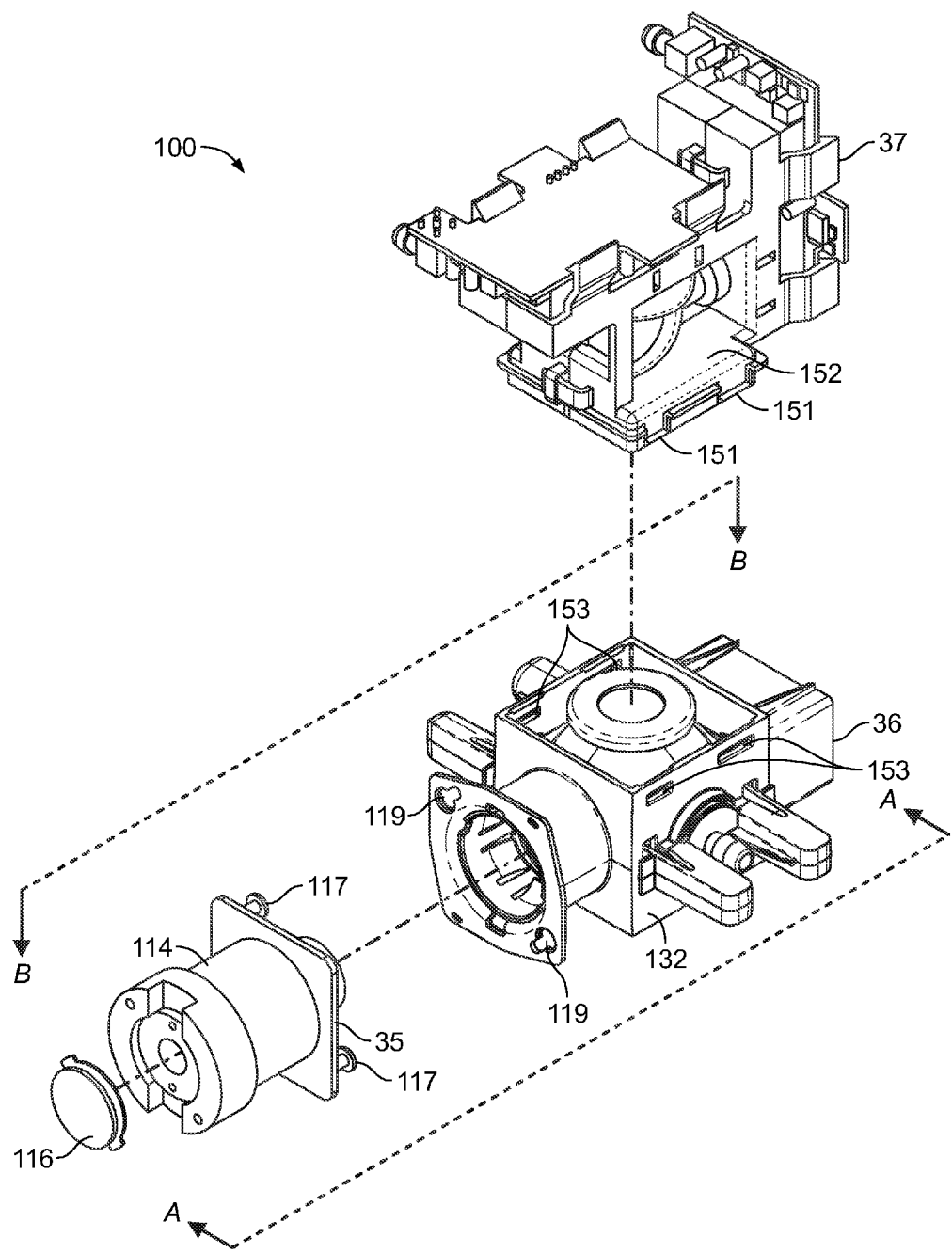
FIG. 2 is a perspective view of a particle detector according to the present invention.

A particle detector 100 according to an embodiment of the invention is shown generally in FIG. 2. It can be broken down into three basic regions, excitation region 35, interrogation region 36 and detection region 37. Excitation region 35 typically includes an excitation light source 116, housing 114 and one or more lenses and filters inside housing 114 as shown in more detail in FIG. 4. Excitation region 35 is also known as the front end assembly due to the fact that it can be assembled as a standalone part that can be attached or removed from the overall particle detector as a single, integrated part using, for example, pins 117 and keyhole slots 119, explained in more detail below.

Interrogation region 36 is where the excitation light interacts with the particles to produce fluorescent and scattering light. Interrogation region 36 typically includes a housing 132 for holding a mirrored chamber, inlet and outlet pitot tubes, and a beam dump to remove any light that does not hit an aerosol particle, as shown in more detail in FIGS. 4 and 5.

Figure 4:
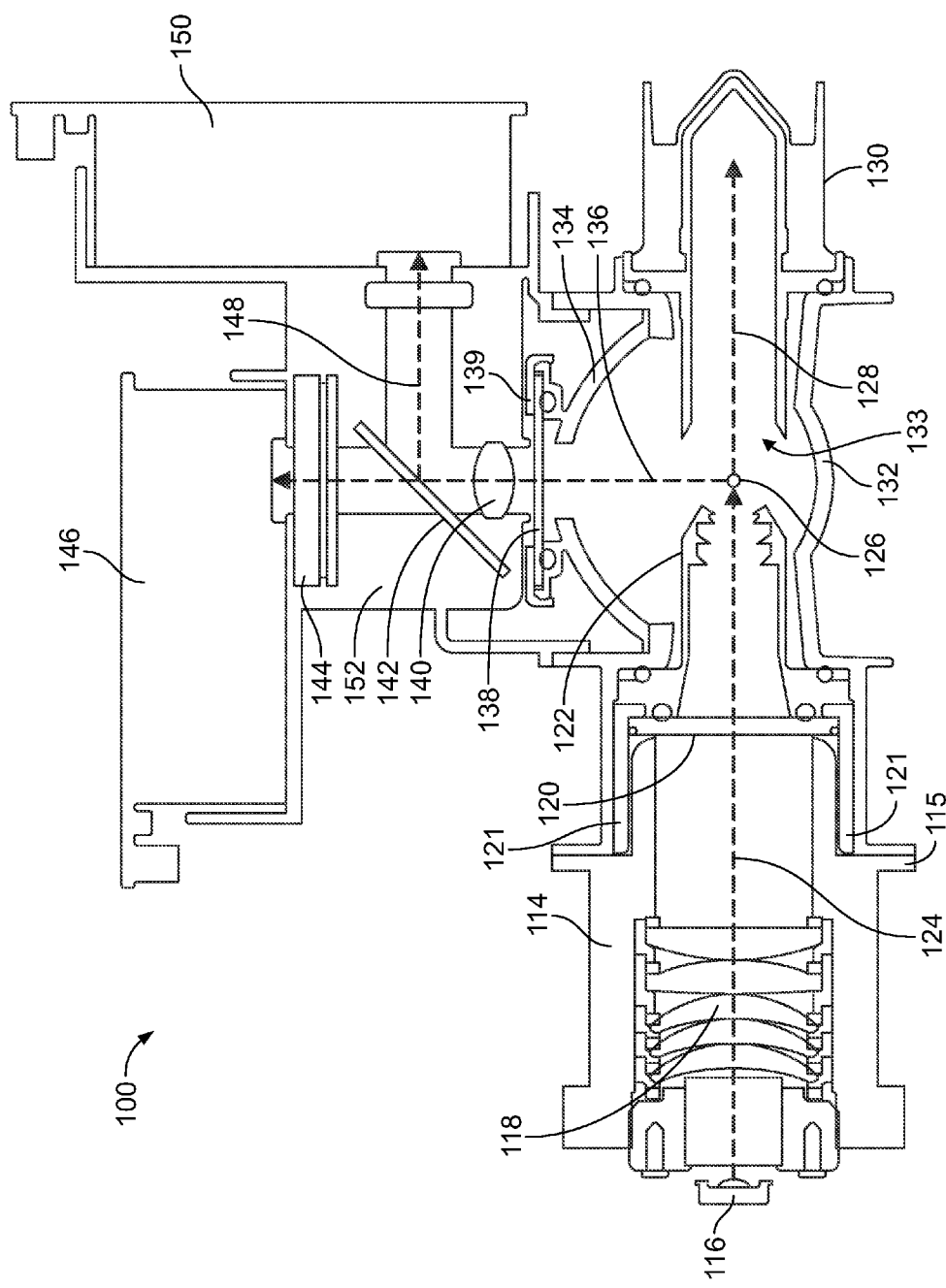
FIG. 4 is side cross section view of a particle detector according to the present invention.
Figure 6:
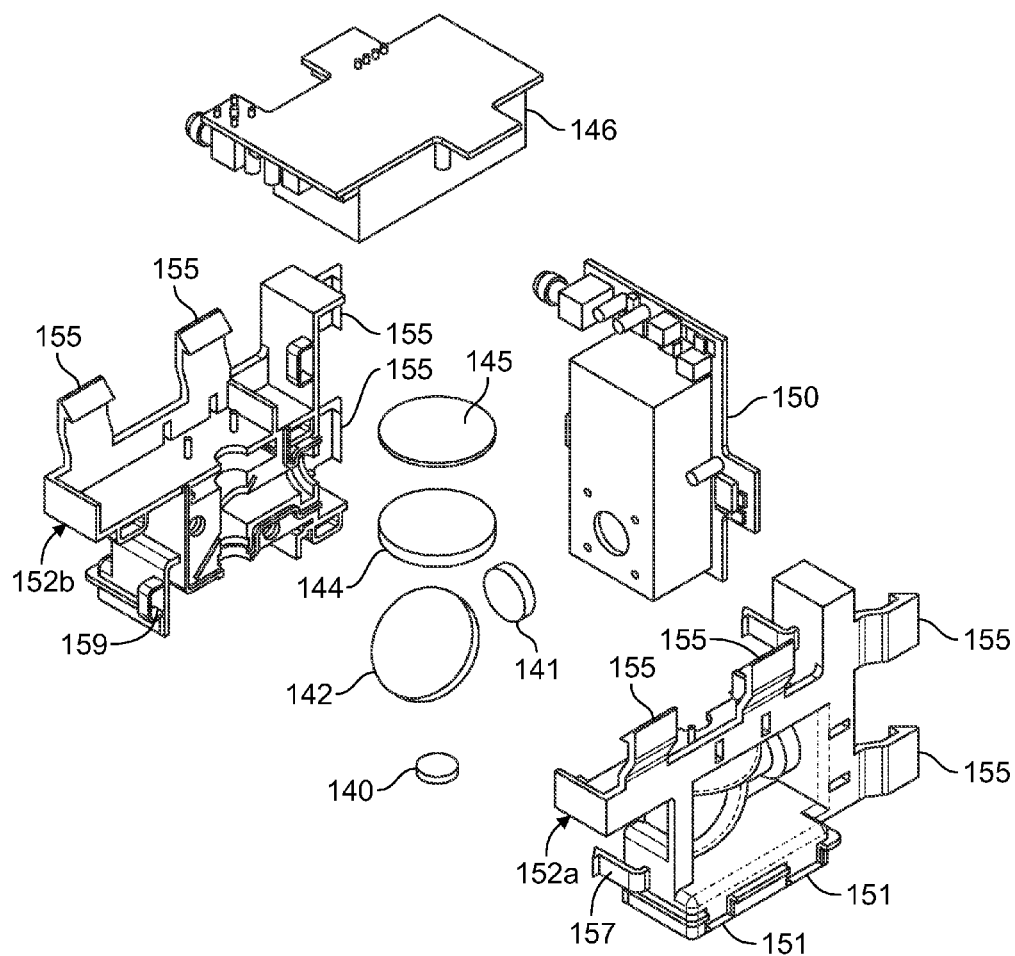
FIG. 6 is an exploded perspective view of the detection region of the particle detector of FIG. 2.

Finally, detection region 37 typically includes lenses, windows, filters to direct an emission beam generated when excitation light hits a particle to optical detectors such as photomultipliers as well as a housing 152 as shown in more detail in FIGS. 4 and 6. The detection region is also known as the back end assembly due to the fact that it can be assembled as a standalone part that can be attached or removed from the overall particle detector as a single, integrated part using tabs 151 and slots 153 described in more detail below.

Figure 3:
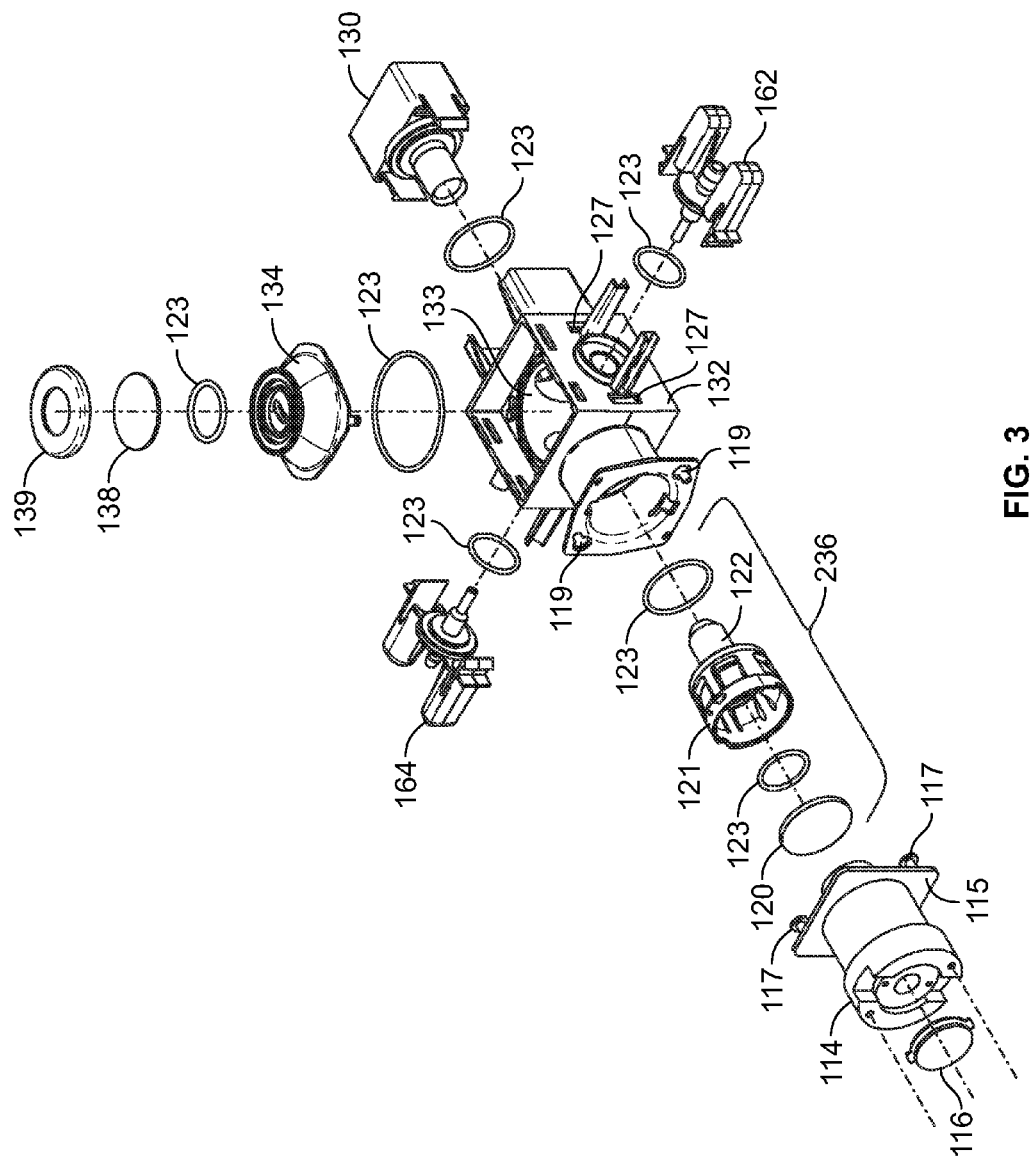
FIG. 3 is an exploded perspective view of excitation and interrogation regions of the particle detector of FIG. 2.

FIG. 3 is an exploded perspective view of the excitation and interrogation regions of particle detector 100. Excitation region 35 includes excitation source 116 and housing 114. Flange 115 includes two or more pins 117 used to attach housing 114 to housing 132 of the interrogation region using keyhole attachments 119. Although a specific embodiment for attachment has been depicted, one of ordinary skill in the art would recognize that several different methods of attaching housings 114 and 132 could be used.

Excitation region 35 further includes spatial aperture assembly 236, which includes tip 122, holder 121 and filter 120. Secure connection between the various components throughout particle detector 100 is provided by O rings 123 as would be understood by one of ordinary skill in the art.

Interrogation region 36 includes housing 132 which connects to several other elements of particle detector 100. Particles are drawn into mirrored chamber 133 through inlet pitot tube 162 by means of a pump (not shown) attached to exhaust pitot tube 164. A lid 134 that is also mirrored fits into housing 134 to form the rest of chamber 133. Filter 138 and cap 139 are attached to lid 134 to form the rest of interrogation region 36. Beam dump 130 is connected to housing 132 opposite excitation region 35. Secure connection between components is provided by O rings 123.

This invention describes a novel plastic-based particle detector design. A design using nylon (polyamide) 66 resin with glass and carbon black fill or similar product produces a functional biological detector. Zytel® ST801AW BK195 by DuPont® is an example of a plastic that has acceptable fluorescence and scattering characteristics. Zytel® will be used as an example of nylon (polyamide) 66 resin with glass and carbon black materials for the balance of this specification but any plastic with similar properties could be used. For balance of this document, the term novel plastic will be used to denote such a plastic.

An optical train made of this plastic has very low fluorescence and scattering, thus providing a particle detector using uncoated plastic components that can detect biological and other materials that fluoresce in the deep UV.

FIG. 4 shows a cross section view of a particle detector 100 along line B of FIG. 2. Excitation region housing 114 holds a light source 116 which generates deep UV light. In an embodiment, light source 116 is a Light Emitting Diode (LED) but a variety of UV light sources could be used. Housing 114 also holds a series of one or more lenses 118 to collect the light. Spatial aperture holder 121 fits over one end of housing 114 to hold short pass filter 120 and a spatial aperture tip 122 which is used to remove stray light. The result is a focused optical beam 124 containing a desired excitation wavelength. In an alternative embodiment, a laser or other techniques for to produce an excitation light beam may be used. Excitation region housing 114 can be injected molded or fabricated from the novel plastic described above.

In this design, an aerosol particle 126 is drawn into detector 100 (as explained in more detail in connection with FIG. 5) such that the excitation light beam 124 intersects with it in a mirrored chamber 133 which forms the main part of interrogation region 36 (as shown in FIG. 2). The interior surfaces of mirrored chamber 133 are coated with a reflective material such as aluminum thus giving them a mirrored surface. Mirrored chamber 133 could be injection molded or otherwise formed from the novel plastic described before.

The detector is designed so that any excitation light 128 not hitting the aerosol particle 126 passes into a beam dump 130 where it is absorbed and removed.

Figure 5:
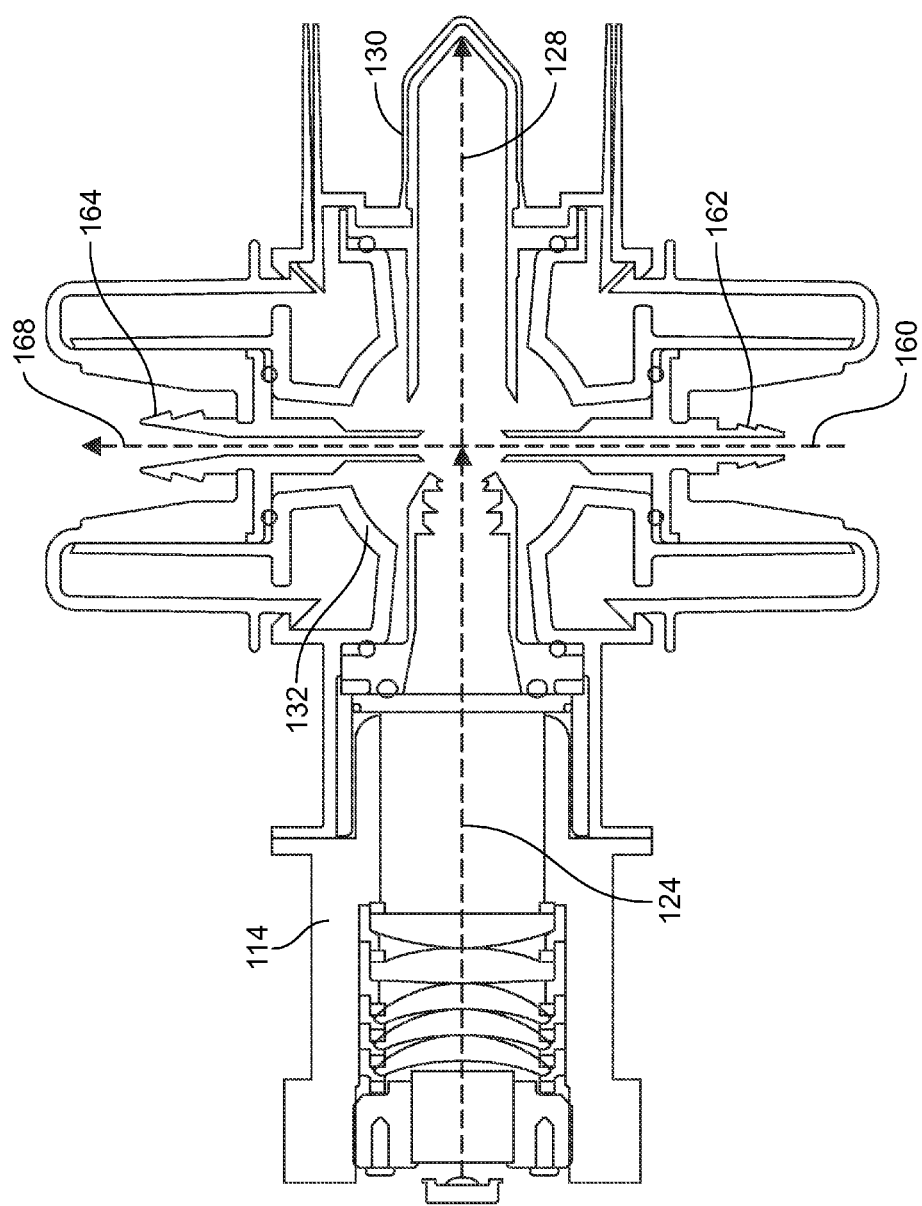
FIG. 5 is a cross section view of the particle detector of FIG. 2.

The mechanism for drawing particles into the particle detector will now be described. A cross section view of particle detector 100 along line A of FIG. 2 is shown in FIG. 5. Aerosol particles 160 are drawn into detector 100 from ambient air via inlet pitot tube 162 by means of a pump (not shown) attached to exhaust pitot tube 164. The flow stream 168 carries aerosol particles through the point where the stream intersects with the excitation beam 124. As also shown in FIG. 2, excitation light 128 not hitting the aerosol particle 126 passes into a beam dump 130 where it is absorbed and removed. Beam dump 130 attaches to housing 132, as does inlet pitot tube 162 and exhaust pitot tube 164 as explained in more detail below. In addition, the parts defining the detection region and housed within detection region housing 152 of FIG. 2 also attach to housing 132 as explained in connection with FIG. 6. Housing 132 can be injected molded or fabricated from the novel plastic described above.

Returning to FIG. 4, when excitation beam 124 hits aerosol particle 126, light 136 is emitted from the particle. This light will typically have both scattering and fluorescence components. The scattering component will be at the same wavelength as the excitation wavelength. The fluorescent component will be at a longer wavelength. If the excitation wavelength is in deep UV range, such as 266-nm, and the aerosol contains UV fluorophores, such as tryptophan, the emission beam 136 will have a fluorescent component, typically in the 350-nm range. Mirrored chamber 133 in housing 132 collects emissions over a collection angle defined by 4 pi steradian. This light increases the intensity of the overall emission 136.

Emission beam 136 passes into detection region 37 (shown in FIG. 2) through filter 138. Filter 138 is held in place by cap 139 and can also be a clear window, such as quartz, that passes all scattering and fluorescent wavelengths. Beam 136 then passes through collection optics 140, beam splitter 142, and filter 144, then finally arrives at photomultiplier 146 which records the intensity of the emission. With the proper selection of these components based on considerations such as their optical band pass and transmissivity, the light reaching photomultiplier 146 contains only the fluorescent component of the total emission from the aerosol particle. Although a specific embodiment has been shown, one of ordinary skill in the art would understand that the filters, optics and beam splitter can be arranged and configured in several different ways.

A portion of emission beam 136 that impacts beam splitter 142 is redirected as beam 148 which arrives at photomultiplier 150. Proper selection of these components based on considerations such as their optical band pass and transmissivity, ensures that the light reaching the photomultiplier 150 contains the scattering component of the total emission from the aerosol particle. It is possible to add filters along the path of beam 148 to attenuate its intensity or remove undesired wavelengths prior to detection by photomultiplier 150. As an alternative, other optical detectors such as avalanche photodiodes can be used in place of one or both of photomultipliers 146 and 150.

Detection region housing 152 captures and holds all the optical parts within the detection region as shown in more detail in FIG. 6. The actual placement of these components can be adjusted as needed and is critical to insure that the focuses and incident angles are optimized to achieve the greatest signal throughput to the PMTs and proper band pass filtering of the scattering and fluorescent light. Detection region housing 152 also forms a pathway by which the emission beam 136 and scattering beam 148 have an open channel to their respective photomultipliers. As shown in FIG. 6, housing 152 is split into two halves 152a and 152b. These halves snap together to hold optical elements 140, 141, 142, 144 and 145 as will be described in more detail below. Photomultipliers, or optical detectors, 146 and 150 are also held by housing 152. Although tabs and slots are shown as a connection mechanism, the specific design and alternatives would be apparent to one of ordinary skill in the art. Housing 152 can be injected molded or fabricated from the novel plastic described above.

There are a number of ways stray light, i.e., light not resulting from impact with an aerosol particle, can be generated in a particle detector. The housings and other materials of the particle detector may have characteristics of fluorescence and scattering independent of light interaction with particles. Several types of undesirable light generation and the solution provided by the present invention are now discussed.

Figure 7:
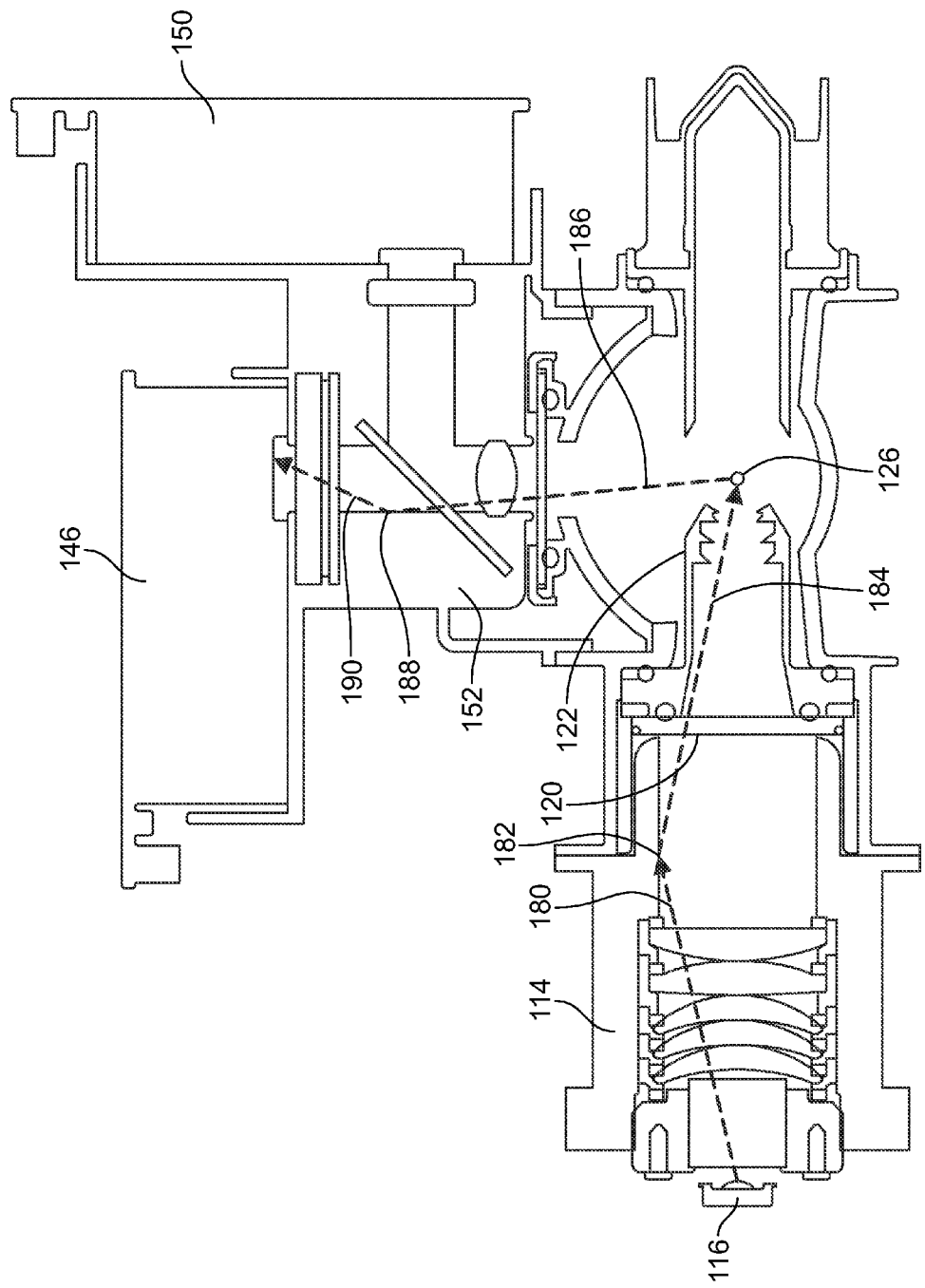
FIG. 7 is view of stray light generation in the particle detector of FIG. 2.

As shown in FIG. 7, light source 116, and especially if it is an LED, often generates stray beams of light 180. This stray light can hit, for example, internal surface 182 of front end housing 114 and result in one or more additional beams 184. Beam 184 could be a scattered light at the same wavelength as that generated by LED 116, one at a longer wavelength due to fluorescence resulting from impact with internal surface 182, or a combination of these.

The selection of materials for excitation region housing 114 is important to minimize the effects from scattering and fluorescence. Prior art designs employ a housing made from metal with a black absorptive coating. According to the present invention, excitation region housing 114 is manufactured from a plastic material that has low and acceptable scattering and fluorescence properties. In a preferred embodiment, Zytel ST801AW BK195 provides an injection moldable means of producing a low cost housing that inherently also forms a means to capture and hold optical components including lenses and filters. This material offers all the manufacturing and cost advantages of using plastic over metal without the impact of high and unusable levels of scattering and fluorescence produced from other plastics. For example, a plastic particle is much lighter than an equivalent particle detector made of metal.

Another common source of stray light arises from the optics of an aerosol detector, also illustrated in FIG. 7. Optic devices such as mirrors and lenses typically have some level of inherent scattering. While it is always the goal to maximize the direct beam paths described in FIG. 4, other beams will often exist. Beam 186 illustrates such a beam. The beam can originate anywhere in the optics. Eventually it will impact a surface as shown, for example, as point 188. Another beam 190 will be produced from this impact that can travel to photomultiplier 146. This signal is normally denoted as a clean-air background signal and, if large enough, can drastically impact the ability to detect the desired emission beam signal 136 triggered by beam 124 of FIG. 4. This is especially true if the impact at point 188 results in fluorescence. Likewise, stray light may be detected as a scattering signal by photomultiplier 150.

As explained above for excitation region housing 114, prior art detectors use a detection region housing 152 fabricated from metal with a black absorptive coating. According to the present invention, detection region housing 152 is manufactured from a plastic that has low and acceptable scattering and fluorescence properties. In a preferred embodiment, Zytel ST801AW BK195 provides an injection moldable means of producing a low cost housing that inherently also forms a means to capture and hold optical components to include lenses and filters. This material offers all the manufacturing and cost advantages of using plastic over metal without the impact of high and unusable levels of scattering and fluorescence produced from other plastics.

Figure 8:
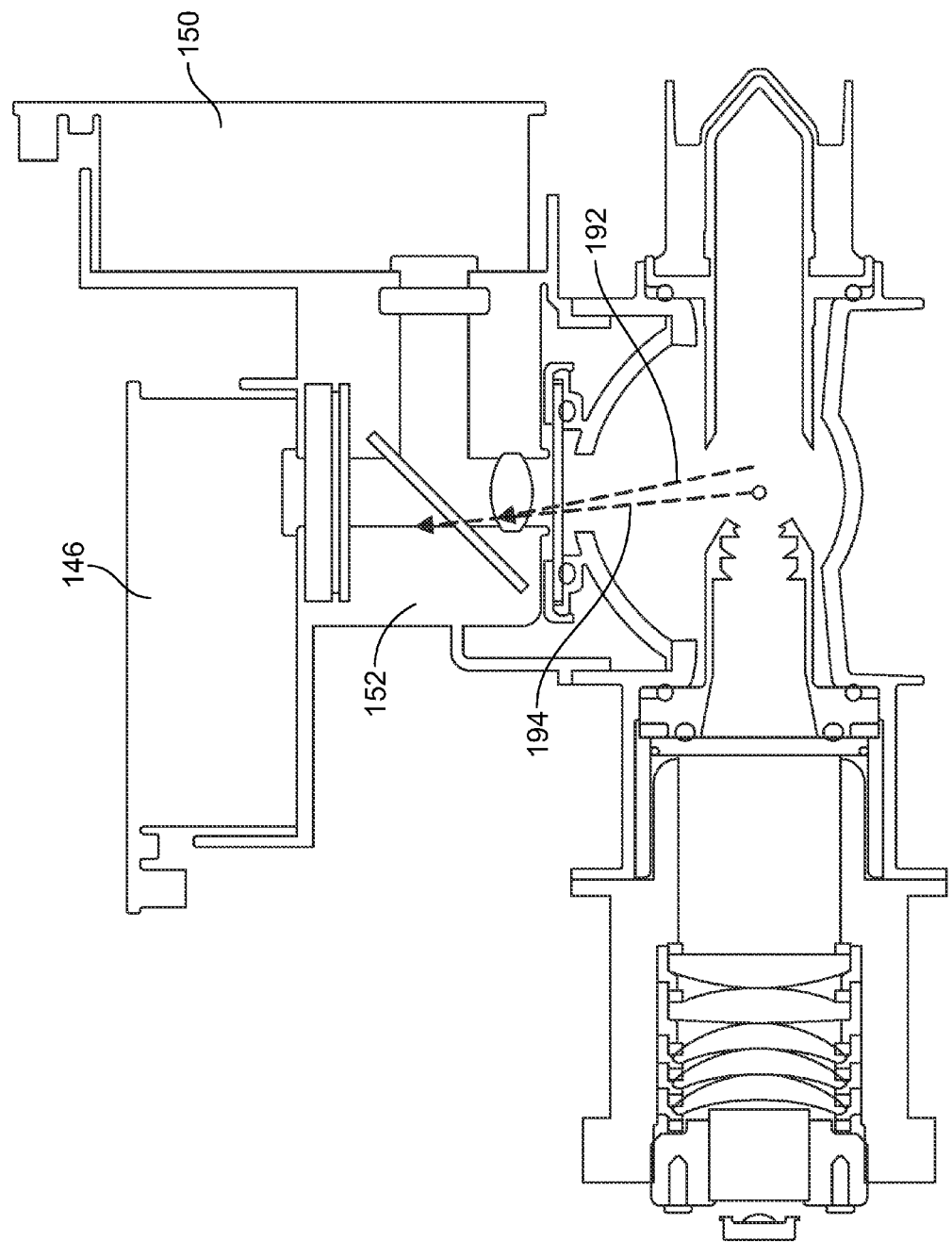
FIG. 8 is view of stray light suppression in the particle detector of FIG. 2.

FIG. 8 illustrates the functionality that can be achieved by using Zytel ST801AW BK195, for example, as the basis for detection region housing 152. This material reduces the scattering and fluorescence signals from stray light beams 192 and 194 to the point that the detector can detect aerosol particles 126 (shown in FIG. 4). The attenuation of the scattering and fluoresce signals has been demonstrated to the point that single sub micron particles have been detected. In contrast, others knowledgeable in the art of detection of biological and other fluorescent aerosols using deep UV light have not used uncoated plastic parts in their designs. This, in part, has been due to the fact that they have not identified a plastic and design that could produce satisfactory scattering and fluorescence characteristics.

There are several benefits realized by the use of the all-plastic detector of the present invention. For example, the various housings of particle detector 100 are designed to snap together using embedded fasteners that are integrally formed with the housings. This reduces assembly time and assembly cost when compared to other materials that may require fasteners. Further, injection molded parts can be designed with intricate details. These details can hold lenses, mirrors and filters. They can also generate spatial filters and baffles. Such details would be costly to reproduce in machined part thus, providing them as part of an integral plastic part also reduces assembly time and cost.

For example, FIGS. 2 and 3 show a connection between housing 114 of excitation region 35 and housing 132 of interrogation region 36 that is formed by pins 117 and keyhole slots 119. Another type of connection is illustrated in FIGS. 2 and 6, which show catches 151 on housing 152 which are inserted into slots 153 on housing 132. FIG. 6 also shows a plurality of catches 155 which are used to attach photomultipliers 146 and 150 to housing 152. At least one catch 157 is inserted into slot 159 so as to attach the two halves of the housing, 152a and 152b, to each other. Although specific embodiments have been shown, variations in shape and design would be understood by one of ordinary skill in the art.

A further benefit of using plastic for a particle detector is that injection molded parts with intricate details to capture optics reduces the number of parts. A lens, for example, could be inserted into a slot designed into the plastic part. It would not require a separate lens hold. This reduces cost while improving ruggedness due to the decrease in the number of parts that can become loose and lose optical alignment. Plastic parts eliminate the potential for corrosion and can also be over-molded to incorporate critical metal parts. This provides a means to insert metal parts into critical regions of the detector with minimum impact to the cost, size and weight. This may be necessary if the detector design requires the use of unique surfaces or structures that can only be achieved on a non-plastic part. Plastic provides a medium by which metal and plastic parts can be easily fused together into a single over-molded part.

Numerous alternative implementations of the present invention exist. For example, this invention can be applied to any optical system requiring a means to reduce stray optical background signal. That includes the telescopes, microscopes and binoculars. It also includes laboratory and office equipment using optical processes, for example, fluorometers, atomic emission spectrometers, Raman spectrometers, optical scanners, and optical readers.

The particle detector 100 in one example comprises a plurality of components which can be combined or divided in the particle detector 100. The particle detector 100 in one example comprises any (e.g., horizontal, oblique, or vertical) orientation, with the description and figures herein illustrating one example orientation of the particle detector 100, for explanatory purposes.

The steps or operations described herein are just for example. There may be many variations to these steps or operations without departing from the spirit of the invention. For instance, the steps may be performed in a differing order, or steps may be added, deleted, or modified.

Although example implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. A particle detector, comprising:
    a excitation region, comprising a first plastic housing and an excitation source for generating light to excite particles passing though the particle detector;
    a interrogation region for producing an emission beam from one or more particles excited by light from the excitation source, comprising a second plastic housing; and
    a detection region for receiving the emission beam, comprising a third plastic housing and one or more optical detectors configured to determine light scattering and fluorescence properties of particles, and
    where the plastic in said first, second, and third plastic housings is a polyamide 66 resin with glass and carbon black fill.

2. The particle detector of claim 1, wherein the first, second and third plastic housings are formed from an uncoated plastic that does not interact with light from the excitation source to produce fluorescent light beams or scattering light beams that will be detected by the one or more optical detectors.

3. The particle detector of claim 1, wherein the first, second and third plastic housings are injection-molded.

4. The particle detector of claim 1, wherein aid first, second and third plastic housings include embedded fasteners so that the housings can be assembled to form the particle detector without additional hardware, glue or welding.

5. The particle detector of claim 1, wherein said excitation region further comprises:
    one or more lenses to collect light from the excitation source fitted into said first housing adjacent to the excitation source; and
    one or more filters fitted into the opposite end of the first housing from the excitation source to remove stray light from the excitation source.

6. The particle detector of claim 1, wherein said interrogation region further comprises:
    a cavity within said second housing, said first housing operatively coupled to one side of said second housing and said third housing operatively coupled to said second housing at a position perpendicular to said first housing; and
    a beam dump operatively coupled to said second housing opposite said first housing.

7. The particle detector of claim 6, wherein said second housing further comprises:
- embedded attachment points that mate with those on the first and third housing;
- embedded attachment points that mate with those on inlet and exhaust pitot tubes on opposite sides of said cavity; and
- embedded attachment points that mate with those on the beam dump.

8. The particle detector of claim 1, wherein the detection region further comprises:
- a beam splitter for splitting the emission beam into two portions;
- a first optical detector configured to determine radiation scattering properties of particles passing through the particle detector according to a first portion of the emission beam; and
- a second optical detector configured to determine fluorescene properties of the particles passing through the particle detector according to a second portion of the emission beam.

9. The particle detector of claim 1, wherein the one or more optical detectors comprise photomultipliers.

10. The particle detector of claim 1, wherein the one or more optical detectors comprise avalanche photodiodes.

11. The particle detector of claim 1, wherein the excitation source generates light in the deep UV wavelength range.

12. A particle detector, comprising:
- a excitation region, comprising:
  - a first plastic housing;
  - an excitation source in one end of said housing;
  - one or more lenses to collect light from the excitation source fitted into said first housing adjacent to the excitation source; and
  - one or more filters fitted into the opposite end of the first housing from the excitation source to remove stray light;
- an interrogation region, comprising:
  - a second plastic housing operatively coupled to said first housing; and
  - a cavity in which one or more particles are excited by light from the excitation source; and
- a detection region, comprising:
  - a third plastic housing operatively coupled to the second housing perpendicularly to said first housing;
  - a first optical detector configured to determine radiation scattering properties of particles passing through the particle detector; and
  - a second optical detector configured to determine fluorescence properties of the particles passing through the particle detector, and
- wherein the plastic in said first, second, and third plastic housings is a polyamide 66 resin with glass and carbon black fill.

13. The particle detector of claim 12, further comprising a beam dump operatively coupled to said second housing opposite said first housing.

14. The particle detector of claim 12, wherein the first, second and third plastic housings are formed from uncoated plastic that does not interact with light from the excitation source to produce fluorescent light beams or scattering light beams that will be detected by the one or more optical detectors.

15. The particle detector of claim 12, wherein the fast, second and third plastic housings are injection-molded.

16. The particle detector of claim 12, wherein said first, second and third plastic housings contain embedded fasteners so that the housings can be assembled to form the particle detector without additional hardware, glue or welding.

17. The particle detector of claim 12, wherein the emission source generates light in the deep UV wavelength range.

18. A method of manufacturing a plastic particle detector, comprising the steps of:
- forming a first housing from plastic, said first housing including molded structures to hold an excitation source and one or more optical devices for focusing light from the excitation source on a particle;
- forming a second housing from plastic, said second housing including molded structures wherein said focused light from said excitation source intersects with said particle and generates an emission beam, said first housing operatively coupled to one side of said second housing; and
- forming a third housing from plastic, said third housing operatively coupled to said second housing perpendicularly to said first housing, said third housing receiving the emission beam and including molded structures for attaching two or more optical detectors; and
- wherein said first, second and third plastic housings comprise a polyamide 66 resin with glass and carbon black fill and contain embedded fasteners so that the housings can be assembled to form the particle detector without additional hardware, glue or welding.

19. The method of claim 18, further comprising the step of:
- forming a beam dump from plastic, said beam dump operatively coupled to said cavity opposite said first housing, without requiring the use of additional fasteners.

20. The method of claim 18, wherein the first, second and third plastic housings are formed from uncoated plastic that does not interact with light from the excitation source to produce fluorescent light beams or scattering light beams that will be detected by the one or morn optical detectors.

21. The method of claim 18, wherein the first, second and third plastic housings we injection-molded.

22. The method of claim 18, where the excitation source generates light in the deep UV wavelength range.

23. The method of claim 18, wherein the one or more optical detectors comprise photomultipliers.

24. The method of claim 18, wherein the one or more optical detectors comprise avalanche photodiodes.

* * * * *